(12) United States Patent
Weinstein (10) Patent No.: US 10,363,240 B2
(45) Date of Patent: *Jul. 30, 2019

(54) COMPOSITIONS AND METHODS FOR TREATING ALOPECIA

(71) Applicant: David Weinstein Consulting, Inc., Dobbs Ferry, NY (US)

(72) Inventor: David Weinstein, Los Altos, CA (US)

(73) Assignee: DAVID WEINSTEIN CONSULTING, INC., Los Altos, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 15/848,628

(22) Filed: Dec. 20, 2017

(65) Prior Publication Data

US 2018/0140577 A1 May 24, 2018

Related U.S. Application Data

(63) Continuation of application No. 15/233,057, filed on Aug. 10, 2016, now abandoned.

(60) Provisional application No. 62/204,799, filed on Aug. 13, 2015, provisional application No. 62/272,180, filed on Dec. 29, 2015, provisional application No. 62/339,398, filed on May 20, 2016.

(51) Int. Cl.
| | |
|---|---|
| *A61K 31/40* | (2006.01) |
| *A61K 31/506* | (2006.01) |
| *A61K 38/13* | (2006.01) |
| *A61K 31/17* | (2006.01) |
| *A61K 31/401* | (2006.01) |
| *A61N 5/06* | (2006.01) |
| *A61N 5/067* | (2006.01) |

(52) U.S. Cl.
CPC .............. *A61K 31/40* (2013.01); *A61K 31/17* (2013.01); *A61K 31/401* (2013.01); *A61K 31/506* (2013.01); *A61K 38/13* (2013.01); *A61N 5/0617* (2013.01); *A61N 2005/067* (2013.01)

(58) Field of Classification Search
None
See application file for complete search history.

(56) References Cited

U.S. PATENT DOCUMENTS

| | | | | |
|---|---|---|---|---|
| 6,331,537 | B1 * | 12/2001 | Hamilton | A61K 31/401 514/215 |
| 2004/0063626 | A1 * | 4/2004 | Kim | A61K 8/64 435/6.16 |
| 2013/0022685 | A1 * | 1/2013 | Sample | A61K 49/0078 424/498 |

OTHER PUBLICATIONS

Gilhar et al., Topical cyclosporine in male pattern alopecia, J Am Acad Dermatol. Feb. 1990;22(2 Pt 1)251-3.
Green et al., Oral cyclosporin does not arrest progression of androgenetic alopecia, Br J Dermatol. Nov. 2001;145 (5);842-5.

* cited by examiner

*Primary Examiner* — Maury A Audet
(74) *Attorney, Agent, or Firm* — Wood, Phillips, Katz, Clark & Mortimer (57) ABSTRACT

The present invention is directed to a composition for treating alopecia containing minoxidil, cyclosporine A and a compound that binds FK506 binding protein 4 suitable for administration to humans. The present invention is further directed to treating alopecia in humans by administering a composition of the invention.

8 Claims, 7 Drawing Sheets
(7 of 7 Drawing Sheet(s) Filed in Color)

5 weeks　　　　　　　　20 weeks

COMPOSITIONS AND METHODS FOR TREATING ALOPECIA

FIELD OF THE INVENTION

The present invention is directed to a composition for treating alopecia containing a compound that binds FK506 binding protein 4 suitable for administration to humans. The present invention is further directed to treating alopecia in humans by administering a composition of the invention.

BACKGROUND OF THE INVENTION

Androgenic alopecia (i.e. male pattern baldness) poses serious psycho-social issues for millions of effected individuals. These individuals include 54% of all US men aged 30 or more and 50 to 75% of US women over the age of 65. Otberg, N., et al., Androgenetic alopecia, *Endocrinology and metabolism clinics of North America*, 2007 June, 36(2), 379-398 and Scheinfeld, N., A review of hormonal therapy for female pattern (androgenic) alopecia, *Dermatology online journal*, 2008. 14(3), 1-5. This translates to more than 150 million individuals in the US alone.

The pathophysiology of androgenic alopecia is not well understood, but as the name implies, testosterone plays a key role in male pattern baldness and hair loss. This role was inferred from the finding that castrated men do not suffer from hair loss. Otberg et al., 2007. Similarly, pseudohermaphrodites that are null at the 5-alpha reductase ("5-AR") loci, which encode for an enzyme involved in testosterone metabolism, are also protected from androgenic alopecia. Ellis J. A., et al., Male pattern baldness: current treatments, future prospects, *Drug Discovery Today*, 2008, 13, 791-797. Testosterone, a lipophilic molecule that diffuses the cell membrane, is converted into its more active form, dihydrotestosterone ("DHT"), by cytoplasmic 5-AR. There are two types of 5-AR, 1 and 2, with type 2 5-AR found in the skin and the inner root sheath of hair follicles. Burkhart C. G., et al., 5 alpha-reductase and finasteride in pattern alopecia and acne, *Journal of Drugs in Dermatology*, 2004, 3, 363-364. Once DHT enters the nucleus it binds to the androgen receptor, regulating gene expression. However, the genes involved in mediating male pattern baldness have yet to be identified.

Only minoxidil, a topically applied compound, and finasteride, an oral medication, have been approved to treat androgenic alopecia. Minoxidil was originally developed as a systemic vasodilating agent to treat hypertension, however many patients suffered with disseminated hypertrichosis as a result of treatment. Bienova M., et al, Androgenetic alopecia and current methods of treatment, *Acta Dermatovenerologica Alpina, Pannonica, et Adriatica*, 2005, 14, 5-8. It was soon discovered that topical application of minoxidil results in limited hair restoration, largely confined to the sites of application. Analysis of the cellular and molecular mechanisms of minoxidil-mediated hair growth has shown that it promotes the survival of dermal papilla cells ("DPCs") of human hair follicles, by activating both ERK and Akt and by preventing cell death by increasing the ratio of Bcl-2/Bax. Han J. H., et al., Effect of minoxidil on proliferation and apoptosis in dermal papilla cells of human hair follicle, *J Dermatol Sci*, 2004, 34, 91-98. The DPCs are thought to provide trophic support to the hair follicle. Rendl M., et al., BMP signaling in dermal papilla cells is required for their hair follicle-inductive properties, *Genes Dev* 2008, 22, 543-557. Among the proteins up-regulated by minoxidil are the trophic factors vascular endothelial growth factor ("VEGF"), hepatocyte growth factor ("HGF"), insulin-like growth factor 1("IGF-1") and bone morphogenic protein 4 ("BMP-4"). Ryu S. et al., Mycophenolate antagonizes IFN-gamma-induced catagen-like changes via beta-catenin activation in human dermal papilla cells and hair follicles, *International Journal of Molecular Sciences* 2014, 15, 16800-16815. Further, minoxidil is known to potentiate HGF and IGF-1 actions through the activation of uncoupled sulfonylurea receptor ("SUR") on the plasma membrane of DPCs. Minoxidil has been shown to be effective in maintaining existing hair follicles, but ineffective in stimulating new follicles. Sinclair has shown that only 15% of those treated with minoxidil had new hair growth, while 50% of those treated maintained existing hair, with no additional loss at 6-months. Sinclair R., Male pattern androgenetic alopecia, BMJ, 1998, 317, 865-869. Notably, discontinuation of minoxidil treatment results in the resumption of hair loss, presumably through the loss of trophic support.

Finasteride, unlike minoxidil, is an oral medication, with potentially severe side effects including erectile dysfunction, gynecomastia, and loss of libido. Finasteride is a competitive 5-AR inhibitor that inhibits the conversion of testosterone to DHT, resulting in a decrease in androgenic alopecia. Price V. H., Treatment of hair loss, *The New England Journal of Medicine*, 1999, 341, 964-973.

In addition to minoxidil and finasteride, cyclosporine A ("CSA"), an immunosuppressive drug intended to prevent rejection of solid organ allografts, promotes robust hair growth in up to 80% of transplant patients receiving systemic treatment. Wysocki G. P., et al., Hypertrichosis in patients receiving cyclosporine therapy, *Clin Exp Dermatol*, 1987, 12, 191-196. While CSA is highly effective in preventing graft rejection, it has severe and undesirable side effects when taken orally or parenterally. Thus, CSA is a poor choice for systemic administration in all but the most life threatening situations. In contrast, the topical administration of low-dose, topical CSA is not associated with immune suppression, hypertension, renal toxicity or the other severe or life-threatening side effects seen with oral CSA administration.

The mechanism of CSA-mediated hair growth was recently elucidated by Fuchs and her colleagues. These workers demonstrated that NFATc1 is expressed preferentially by the follicular stem cell, where it acts to repress stem cell proliferation. Upon administration, CSA binds to the calmodulin-dependent, serine/threonine protein phosphatase calcineurin, which in turn binds to NFAT, and relieves the repression on the follicular stem cell. With the NFAT repression relieved, the follicular stem cells proliferate, resulting in precocious follicular growth. Horsley V., et al., NFATc1 balances quiescence and proliferation of skin stem cells, *Cell*, 2008, 132, 299-310. Interestingly, as opposed to oral administration, topical treatment with CSA has shown to be very inefficient at promoting hair growth in androgenic alopecia when used alone, or in combination with minoxidil. Gilhar A., et al., Topical cyclosporine in male pattern alopecia, *J Am Acad Dermatol*, 1990, 22, 251-253; Buhl A. E., et al., Differences in activity of minoxidil and cyclosporin A on hair growth in nude and normal mice. Comparisons of in vivo and in vitro studies, *Laboratory Investigation; A Journal of Technical Methods and Pathology*, 1990, 62, 104-107.

Another compound that has shown hair growth stimulation is RT175 (AMG-474-00, GM1485, GPI 1485). RT175 is a 241 Dalton molecule having the following chemical structure RT175 has been shown to re-grow hair in rats that have undergone craniotomy prior to neurosurgery. Ducruet et al., GM1485, a nonimmunosuppressive immunophilin ligand, promotes neurofunctional improvement and neural regeneration following stroke, *J Neurosci Res,* 2012 July, 90(7): 1413-23. RT175 has also been shown to induce hair growth in shaved mice. European Patent No. 1842845 to GliaMed, Inc., published Oct. 10, 2007. RT175 binds with high affinity to FK506 binding protein 4 ("FKBP52"). FKBP52 is known to act as a molecular chaperone for the glucocorticoid receptor ("GR"). After binding to ligand, the RT175/GR complex translocates to the nucleus. Banerjee A., et al. Control of glucocorticoid and progesterone receptor subcellular localization by the ligand-binding domain is mediated by distinct interactions with tetratricopeptide repeat proteins, *Biochemistry,* 2008, 47, 10471-10480. It has been shown that that RT175 treatment of fibroblasts for 2 hours results in the translocation of FKBP52 to the nucleus, presumably with its cargo. This timeframe is consistent with cDNA array studies that have shown a significant upregulation of chromatin remodeling via the transcription factors Ikaros and Afq1, suggesting that treatment with RT175 results in alteration in chromatin structure as the cells are reprogrammed, including the up-regulation of secreted molecules that are associated with hair growth, wnt1 and IGF2. Keshava C., et al., Transcriptional signatures of environmentally relevant exposures in normal human mammary epithelial cells: benzo[a]pyrene, *Cancer Letters,* 2005, 221, 201-211; Koipally J., et al. Ikaros chromatin remodeling complexes in the control of differentiation of the hemolymphoid system, *Cold Spring Harb Symp Quant Biol* 1999, 64, 79-86; Galbiati F., et al., Caveolin-1 expression inhibits Wnt/beta-catenin/Lef-1 signaling by recruiting beta-catenin to caveolae membrane domains, *J Biol Chem,* 2000, 275, 23368-23377; Tamimi Y. et al., WNT5A is regulated by PAX2 and may be involved in blastemal predominant Wilms tumorigenesis, *Neoplasia,* 2008, 10, 1470-1480; Nakao K., et al., IGF2 modulates the microenvironment for osteoclastogenesis, *Biochem Biophys Res Commun,* 2009, 378, 462-466; Sun Y., et al., Evolutionarily conserved transcriptional co-expression guiding embryonic stem cell differentiation, *PLoS ONE,* 2008, 3, e3406; Andl T., et al., WNT signals are required for the initiation of hair follicle development, *Developmental Cell,* 2002, 2, 643-653.

Despite the commercial availability of minoxidil and finasteride and demonstrations of hair growth following systemic administration of cyclosporine A and topical administration of RT175 in rodents there remains a need in the art for a topical composition for the treatment of alopecia in humans that avoids the side effects of oral or parenteral administration and is long-lasting.

SUMMARY OF THE INVENTION

In one aspect, the present invention is directed to a composition for the treatment of alopecia comprising a compound that binds FK506 binding protein 4.

In another aspect, the present invention is directed to a composition for the treatment of alopecia comprising a compound that binds FK506 binding protein 4 and one or more additional active agents selected from the group consisting of minoxidil, cyclosporine A, and a combination thereof.

In another aspect, the present invention is directed to a composition for the treatment of alopecia comprising a compound of formula (I)

or a pharmaceutically acceptable salt or ester thereof, minoxidil and cyclosporine A, wherein $R^1$ is COOH, a methoxy, a phenyl, a benzyl, a substituted phenyl or a substituted benzyl.

In a preferred embodiment the substituted phenyl and substituted benzyl of the compound of formula (I) are each individually substituted with an alkyl group, a methoxy group or a halogen.

In a more preferred embodiment the compound of formula (I) is selected from the group consisting of

("RT175"), ("RT1061"),

("RT1062") and ("RT1063") and a pharmaceutically acceptable salt or ester thereof.

In a most preferred embodiment the compound of formula (I) is RT175.

In another aspect, the present invention is directed to a composition for the treatment of alopecia comprising a compound of formula (II)

or a pharmaceutically acceptable salt or ester thereof, minoxidil and cyclosporine A.

In another more preferred aspect, the compositions of the present invention further comprise one or more excipients selected from the group consisting of urea, polyoxyl 40 stearate, a carbomer, cetyl alcohol, glyceryl monostearate, mineral oil, ethanol, propylene glycol, polyglycol 300, citric acid, sodium phosphate dibasic, stearyl alcohol, isopropyl myristate, sodium hydroxide, petroleum jelly, xanthan gum, white petrolatum, sorbitol solution, cetearyl alcohol, ceteareth-20, simethicone, sodium benzoate, glyceryl monostearate, polyethylene glycol monostearate, sorbic acid, butylated hydroxytoluene and water.

In a preferred embodiment the one or more excipients are a combination of white petrolatum, sorbitol solution, propylene glycol, cetearyl alcohol, ceteareth-20, simethicone, glyceryl monostearate, polyethylene glycol monostearate, sorbic acid and butylated hydroxytoluene.

In another preferred embodiment, the one or more excipients are a combination of urea, polyoxyl 40 stearate, propylene glycol, polyglycol 300 (Medibase C available from Medisca), citric acid, sodium phosphate dibasic, cetyl alcohol, stearyl alcohol, isopropyl myristate, sodium benzoate and water.

In a more preferred embodiment, the one or more excipients are a combination of about 1,200 grams of urea, about 103 grams polyoxyl 40 stearate, about 63 milliliters of propylene glycol, about 47 milliliters of polyglycol 300, about 1 gram of citric acid, about 2 grams of sodium phosphate, about 94 grams of cetyl alcohol, about 200 grams of stearyl alcohol, about 219 grams of isopropyl myristate, about 3 grams of sodium benzoate and about 1,000 to about 1,500 milliliters of water.

In a preferred aspect, the present invention is directed to a composition for the treatment of alopecia comprising minoxidil at a concentration from about 1% to about 10% w/v, cyclosporine A at a concentration from about 0.01% to about 1% w/v and RT175 at a concentration from about 0.000001% to about 0.0001% w/v.

In another preferred aspect, the present invention is directed to a composition for the treatment of alopecia comprising minoxidil at a concentration from about 1% to about 10% w/v, cyclosporine A at a concentration from about 0.01% to about 1% w/v, RT175 or a pharmaceutically acceptable salt or ester thereof at a concentration from about 0.000001% to about 0.0001% w/v, ethanol at a concentration from about 10% to about 50% w/v, propylene glycol at a concentration from about 10% to about 70% w/v and water at a concentration from about 10% to about 50% w/v.

In a more preferred aspect, the present invention is directed to a composition for the treatment of alopecia comprising minoxidil at a concentration of about 5% w/v, cyclosporine A at a concentration of about 0.12% w/v and RT175 or a pharmaceutically acceptable salt or ester thereof at a concentration of about 0.000012% w/v.

In another more preferred aspect, the present invention is directed to a composition for the treatment of alopecia comprising minoxidil at a concentration of about 5% w/v, cyclosporine A at a concentration of about 0.12% w/v, RT175 or a pharmaceutically acceptable salt or ester thereof at a concentration of about 0.000012% w/v, ethanol at a concentration of about 28% w/v, propylene glycol at a concentration of about 47% w/v and water at a concentration of about 19% w/v.

In another aspect, the present invention is directed to a method of treating alopecia comprising topically administering to a human in need thereof an effective amount of a composition of the present invention.

In a preferred aspect, the present invention is directed to a method of treating androgenic alopecia comprising topically administering to a human in need thereof an effective amount of a composition of the present invention.

In another aspect, the present invention is directed to a method of treating alopecia in a human in need thereof comprising topically administering concurrently or sequentially minoxidil, cyclosporine A and a compound that binds FK506 binding protein 4.

In a preferred aspect, the human in need of alopecia treatment suffers from achromotrichia and the method provides regrowth of pigmented hair, preferably the achromotrichia is due to aging.

In another aspect, the present invention is directed to a method of enhancing facial hair (including eye brow) growth comprising topically administering to a human in need thereof an effective amount of the compositions of the present invention.

In a preferred aspect, the present invention is directed to a method of treating alopecia in a human in need thereof comprising topically administering concurrently or sequentially minoxidil at a concentration from about 1% to about 10% w/v, cyclosporine A at a concentration from about 0.01% to about 1% w/v and RT175 or a pharmaceutically acceptable salt or ester thereof at a concentration from about 0.000001% to about 0.0001% w/v.

In a more preferred aspect, the present invention is directed to a method of treating alopecia in a human in need thereof comprising topically administering concurrently or sequentially minoxidil at a concentration of about 5% w/v, cyclosporine A at a concentration of about 0.12% w/v and RT175 or a pharmaceutically acceptable salt or ester thereof at a concentration of about 0.000012% w/v.

In a more preferred aspect, the present invention is directed to a method of treating alopecia in a human in need thereof comprising topically administering to a human in need thereof an effective amount of the composition comprising minoxidil, cyclosporine and RT175 or a pharmaceutically acceptable salt or ester thereof, and urea.

In another aspect the present invention is directed to a method of treating alopecia in a human in need thereof comprising the steps of:
(i) administering fractional laser treatment to an affected area of a human; and
(ii) topically administering a composition of the invention, wherein the steps can be in any order.

In another aspect the present invention is directed to a method of treating alopecia in a human in need thereof comprising the steps of:
(i) pretreating an area affected with alopecia with 40% w/v urea; and
(ii) topically administering a composition of the invention.

In another aspect, the present invention is directed to a method of treating alopecia comprising topically administering concomitantly or sequentially a compound that binds FK506 binding protein 4 and at least one compound selected from the group consisting of minoxidil and cyclosporine A.

In another aspect, the present invention is directed to a method of treating alopecia comprising topically administering concomitantly or sequentially a compound that binds FK506 binding protein 4, minoxidil and cyclosporine A.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Applicants unexpectedly discovered a composition for the treatment of alopecia which has reduced side effects and prolonged effects over available treatments.

As used herein, "minoxidil" refers to the compound of the formula, and any pharmaceutically acceptable salt or ester thereof.

As used herein, "cyclosporine A" refers to the compound of the formula, and any pharmaceutically acceptable salt or ester thereof.

As used herein, "RT175" refers to the compound of the formula,

As used herein, "alopecia" refers to the loss of hair from the body, whether on the scalp, body, face or eyebrows, and due to a pathological condition.

As used herein the term "pharmaceutically acceptable" refers to ingredients that are not biologically or otherwise undesirable in a topical application.

As used herein the term "effective amount" refers to the amount necessary to treat a patient in need thereof.

As used herein, "androgenic alopecia" refers to an autosomal disorder which begins in puberty in genetically disposed individuals. Androgenic alopecia is also known as hereditary baldness, male pattern baldness, and seborrheic alopecia. Androgenic alopecia may occur in males and females.

As used herein, "achromotrichia" refers to an absence or loss of pigment in the hair shaft. Achromotrichia may be due to aging, stress, diet or disease.

As used herein, "fractional laser therapy" or "fractional laser treatment" refers to application of a laser beam that is divided into thousands of zones and is capable of reacting with both the epidermis and dermis. This treatment is sometimes referred to as fractional laser photothermolysis. Fractional lasers may be based on, but are not limited to, erbium, carbon dioxide, diode, yttrium aluminum garnet (YAG), neodymium-doped yttrium aluminum garnet, yttrium scandium gallium garnet (YSGG) or combinations thereof. Commercial examples of fractional lasers sufficient for the present invention include, but are not limited to, Profractional (Sciton, Inc.), Halo (Sciton, Inc.), Emerge (Cynosure Palomar), Lux1540 (Cynosure Palomar), Lux2940 (Cynosure Palomar), Deep FX (Lumenis), Active FX (Lumenis), Fraxel Re:pair® (Fraxel re:pair is a registered trademark of Reliant Technologies LLC; available through Solta Medical), Fraxel Re:store® (Fraxel re:store is a registered trademark of Reliant Technologies LLC; available through Solta Medical), Clear+Brilliant (Solta Medical), Fraxel® Dual 1550/1027 (Fraxel® is a registered trademark of Reliant Technologies LLC; available through Solta Medical) and Pearl® Fractional (Pearl is a registered trademark of Cutera, Inc.).

As used herein, "treatment" or "treating" refers to preventing hair loss and growing, regrowing and regenerating hair. As used herein the term "pharmaceutically acceptable" refers to ingredients that are not biologically or otherwise undesirable in a topical application.

As used herein the term "effective amount" refers to the amount necessary to treat a patient in need thereof.

As used herein "% w/v" and "percent w/v" refer to the percent weight of the total formulation.

As used herein the term "$R^1$" refers to a substituent selected from the group consisting of COOH, a methoxy, a phenyl, a benzyl, a substituted phenyl and a substituted benzyl.

In general, the term "substituted" means that one or more hydrogens of the designated moiety are replaced with a suitable substituent.

As used herein the term "alkyl" refers to a branched or straight-chain alkyl consisting of a saturated hydrocarbon group of 1 to 24 carbon atoms ($C_1$-$C_{24}$) unless otherwise stated. The alkyl group can be cyclic or acyclic. As used herein, all numerical values relating to amounts, weights, and the like, that are defined as "about" each particular value is plus or minus 10%. For example, the phrase "about 10% w/v" is to be understood as "9% to 11% w/v." Therefore, amounts within 10% of the claimed value are encompassed by the scope of the claims.

In some embodiments, compositions of the present invention may contain a solvent. Solvents of the present invention include, but are not limited to, ethanol, propylene glycol, water, polyethylene glycol, glycerol, isostearic acid, oleic acid, trolamine, tromethamine, triacetin, sorbitan monolaurate, sorbitan monooleate, sorbitan monopalmitate, butanol, iso-amyl acetate, methanol, propanol, isobutene, pentane, hexane, chlorobutanol, turpentine, cytopentasiloxane, cyclomethicone, methyl ethyl ketone and mixtures thereof. Total solvents of the present invention may be at concentrations from about 10% to about 99% w/v, preferably from about 50% to about 99% w/v and more preferably from about 80% to about 95% w/v. In a preferred embodiment, the solvent is a mixture of ethanol, propylene glycol and water, more preferably from about 10% to about 50% w/v ethanol, from about 10% to about 70% w/v propylene glycol and from about 10% to about 50% w/v water and even more preferably about 28% w/v ethanol, about 47% w/v propylene glycol and about 19% w/v water.

In one embodiment, the present invention is directed to a composition for the treatment of alopecia comprising a compound that binds FK506 binding protein 4.

In another embodiment, the present invention is directed to a composition for the treatment of alopecia comprising a compound that binds FK506 binding protein 4 and one or more additional active agents selected from the group consisting of minoxidil, cyclosporine A, and a combination thereof.

In another embodiment, the present invention is directed to a composition for the treatment of alopecia comprising a compound of formula (I) or a pharmaceutically acceptable salt or ester thereof, minoxidil and cyclosporine A, wherein R1 is COOH, a methoxy, a phenyl, a benzyl, a substituted phenyl or a substituted benzyl.

In a preferred embodiment the substituted phenyl and substituted benzyl of the compound of formula (I) are each individually substituted with an alkyl group, a methoxy group or a halogen.

In a more preferred embodiment the compound of formula (I) is selected from the group consisting of ("RT175"), ("RT1061"), ("RT1062") and ("RT1063") and a pharmaceutically acceptable salt or ester thereof.

In a most preferred embodiment the compound of formula (I) is RT175.

In another embodiment, the present invention is directed to a composition for the treatment of alopecia comprising a compound of formula (II) or a pharmaceutically acceptable salt or ester thereof, minoxidil and cyclosporine A.

In another more preferred aspect, the compositions of the present invention further comprise one or more excipients selected from the group consisting of urea, polyoxyl 40 stearate, a carbomer, cetyl alcohol, glyceryl monostearate, mineral oil, ethanol, propylene glycol, polyglycol 300, citric acid, sodium phosphate dibasic, stearyl alcohol, isopropyl myristate, sodium hydroxide, petroleum jelly, xanthan gum, white petrolatum, sorbitol solution, cetearyl alcohol, ceteareth-20, simethicone, sodium benzoate, glyceryl monostearate, polyethylene glycol monostearate, sorbic acid, butylated hydroxytoluene and water.

In a preferred embodiment the one or more excipients are a combination of white petrolatum, sorbitol solution, propylene glycol, cetearyl alcohol, ceteareth-20, simethicone, glyceryl monostearate, polyethylene glycol monostearate, sorbic acid and butylated hydroxytoluene.

In another preferred embodiment, the one or more excipients are a combination of urea, polyoxyl 40 stearate, propylene glycol, polyglycol 300 (Medibase C available from Medisca), citric acid, sodium phosphate dibasic, cetyl alcohol, stearyl alcohol, isopropyl myristate, sodium benzoate and water.

In a more preferred embodiment, the one or more excipients are a combination of about 1,200 grams of urea, about 103 grams polyoxyl 40 stearate, about 63 milliliters of propylene glycol, about 47 milliliters of polyglycol 300, about 1 gram of citric acid, about 2 grams of sodium phosphate, about 94 grams of cetyl alcohol, about 200 grams of stearyl alcohol, about 219 grams of isopropyl myristate, about 3 grams of sodium benzoate and about 1,000 to about 1,500 milliliters of water.

In a preferred embodiment, the present invention is directed to a composition for the treatment of alopecia comprising minoxidil at a concentration from about 1% to about 10% w/v, cyclosporine A at a concentration from about 0.01% to about 1% w/v and RT175 at a concentration from about 0.000001% to about 0.0001% w/v.

In another preferred embodiment, the present invention is directed to a composition for the treatment of alopecia comprising minoxidil at a concentration from about 1% to about 10% w/v, cyclosporine A at a concentration from about 0.01% to about 1% w/v, RT175 or a pharmaceutically acceptable salt or ester thereof at a concentration from about 0.000001% to about 0.0001% w/v, ethanol at a concentration from about 10% to about 50% w/v, propylene glycol at a concentration from about 10% to about 70% w/v and water at a concentration from about 10% to about 50% w/v.

In a more preferred embodiment, the present invention is directed to a composition for the treatment of alopecia comprising minoxidil at a concentration of about 5% w/v, cyclosporine A at a concentration of about 0.12% w/v and RT175 or a pharmaceutically acceptable salt or ester thereof at a concentration of about 0.000012% w/v.

In another more preferred embodiment, the present invention is directed to a composition for the treatment of alopecia comprising minoxidil at a concentration of about 5% w/v, cyclosporine A at a concentration of about 0.12% w/v, RT175 or a pharmaceutically acceptable salt or ester thereof at a concentration of about 0.000012% w/v, ethanol at a concentration of about 28% w/v, propylene glycol at a concentration of about 47% w/v and water at a concentration of about 19% w/v.

In another embodiment, the present invention is directed to a method of treating alopecia comprising topically administering to a human in need thereof an effective amount of a composition of the present invention.

In a preferred embodiment, the present invention is directed to a method of treating androgenic alopecia comprising topically administering to a human in need thereof an effective amount of a composition of the present invention.

In another embodiment, the present invention is directed to a method of treating alopecia in a human in need thereof comprising topically administering concurrently or sequentially minoxidil, cyclosporine A and a compound that binds FK506 binding protein 4.

In a preferred embodiment, the human in need of alopecia treatment suffers from achromotrichia and the method provides regrowth of pigmented hair, preferably the achromotrichia is due to aging.

In another embodiment, the present invention is directed to a method of enhancing facial hair growth (including but not limited to eye brows) comprising topically administering to a human in need thereof an effective amount of the compositions of the present invention.

In a preferred embodiment, the present invention is directed to a method of treating alopecia in a human in need thereof comprising topically administering concurrently or sequentially minoxidil at a concentration from about 1% to about 10% w/v, cyclosporine A at a concentration from about 0.01% to about 1% w/v and RT175 or a pharmaceutically acceptable salt or ester thereof at a concentration from about 0.000001% to about 0.0001% w/v.

In a more preferred embodiment, the present invention is directed to a method of treating alopecia in a human in need thereof comprising topically administering concurrently or sequentially minoxidil at a concentration of about 5% w/v, cyclosporine A at a concentration of about 0.12% w/v and RT175 or a pharmaceutically acceptable salt or ester thereof at a concentration of about 0.000012% w/v.

In another embodiment the present invention is directed to a method of treating alopecia in a human in need thereof comprising the steps of:
(i) administering fractional laser treatment to an affected area of a human; and
(ii) topically administering a composition of the invention,
wherein the steps can be in any order.

In another embodiment the present invention is directed to a method of treating alopecia in a human in need thereof comprising the steps of:
(i) pretreating an area affected with alopecia with 40% w/v urea; and
(ii) topically administering a composition of the invention.

In another embodiment, the present invention is directed to a method of treating alopecia comprising topically administering concomitantly or sequentially a compound that binds FK506 binding protein 4 and at least one compound selected from the group consisting of minoxidil and cyclosporine A.

In another embodiment, the present invention is directed to a method of treating alopecia comprising topically administering concomitantly or sequentially a compound that binds FK506 binding protein 4, minoxidil and cyclosporine A.

In a preferred embodiment, the present invention is directed to a composition for the treatment of alopecia comprising minoxidil at a concentration of about 5% w/v, cyclosporine A at a concentration of about 0.12% w/v and RT175 or a pharmaceutically acceptable salt or ester thereof, an analog thereof or a derivative thereof at a concentration of about 0.000012% w/v.

In another preferred embodiment, the present invention is directed to a composition for the treatment of alopecia comprising minoxidil at a concentration of about 5% w/v, cyclosporine A at a concentration of about 0.12% w/v, RT175 or a pharmaceutically acceptable salt or ester thereof, an analog thereof or a derivative thereof at a concentration of about 0.000012% w/v, ethanol at a concentration of about 28% w/v, propylene glycol at a concentration of about 47% w/v and water at a concentration of about 19% w/v.

In a preferred embodiment, the present invention is directed to a composition for the treatment of alopecia comprising minoxidil at a concentration of about 5% w/v, cyclosporine A at a concentration of about 0.12% w/v, RT175 or a pharmaceutically acceptable salt or ester thereof, an analog thereof or a derivative thereof at a concentration of about 0.000012% w/v, and one or more excipients selected from the group consisting of urea, a carbomer, cetyl alcohol, glyceryl monostearate, mineral oil, propylene glycol, sodium hydroxide, petroleum jelly, xanthan gum and water, in a preferred embodiment the urea is at a concentration of about 40% w/v.

In another preferred embodiment, the present invention is directed to a composition for the treatment of alopecia comprising minoxidil, cyclosporine A, RT175 or a pharmaceutically acceptable salt or ester thereof, an analog thereof or a derivative thereof and one or more excipients selected from the group consisting of urea, a carbomer, cetyl alcohol, glyceryl monostearate, mineral oil, propylene glycol, sodium hydroxide, petroleum jelly, xanthan gum and water. In this preferred embodiment the urea is at a concentration of about 40% w/v.

The formulating of the immediate above preferred embodiment may include the following:

weigh out 100 g 40% urea cream comprising X-Viate™ 40% cream: 40 g urea (w/v), carbopol, cetyl alcohol, glyceryl monostearate, light mineral oil, propylene glycol, water, sodium hydroxide, white petrolatum and xanthum gum; or emollient cream #1: 40 g urea plus 60 g emollient cream #1 (polyoxyl 40 stearate (103.125 g/L), propylene glycols (62.2 ml/L), polyglycol 300 MW liquid (46.875 ml/L), citric acid-anhydrous (1.1 g/L), sodium phosphate dibasic (2.04 g/L), cetyl alcohol wax (93.75 g/L), stearyl alcohol wax (200 g/L), isopropyl myristate (218.75/L), dd $H_2O$ to 1 L; sodium benzoate (3.125 g/L)); add 5 g minoxidil powder and then add 120 mg cyclosporine A powder or 120 mg cyclosporine A dissolved in 2 ml propylene glycol; followed by adding 50 μl of a 1M solution RT175 (>120 ng/ml final); and then mixing the resultant composition and loading it into 20 ml syringes or into tubes for dispensing.

EXAMPLES

Example 1. Punch Biopsies of Mouse Dorsal Skin Treated Topically with RT175

Mice underwent 5 millimeter, full thickness, punch biopsies of their dorsal skin. Mice were then treated topically with 120 nanograms ("ng") of RT175, daily.

Figure 1:
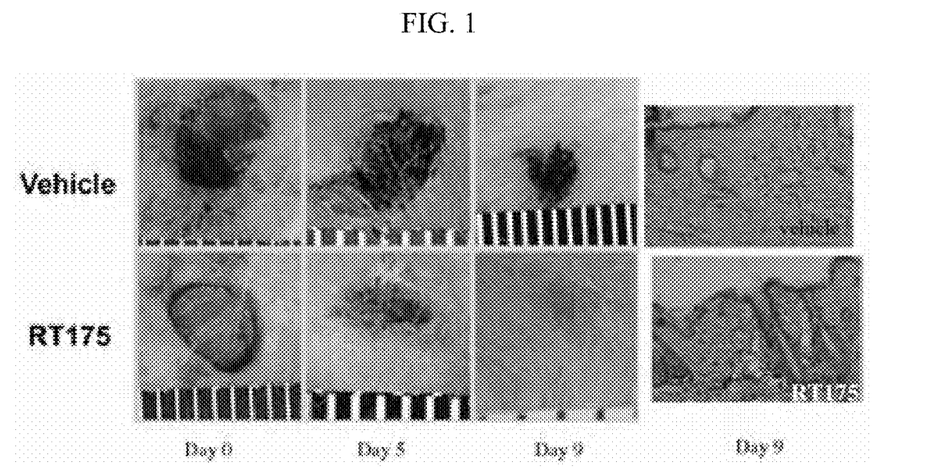
FIG. 1. Punch biopsies of mouse dorsal skin treated topically with RT175.

5 days after punch biopsy healing of the wound site is clearly accelerated in mice receiving RT175 over vehicle. See FIG. 1. 9 days after punch biopsy 80% of the RT175 treated wounds are completely closed. The other 20% of RT175 treated wounds closed within 18 hours. Additionally, 9 days after punch biopsy the RT175 treated wounds displayed robust hair regeneration, with intact follicles even in the middle of the wound. See FIG. 1. By comparison, the vehicle treated tissue has yet to regenerate follicles in the center of the wound site.

Example 2. Scalp Closure Following Craniotomy in Rats Treated Topically with RT175

Figure 2:
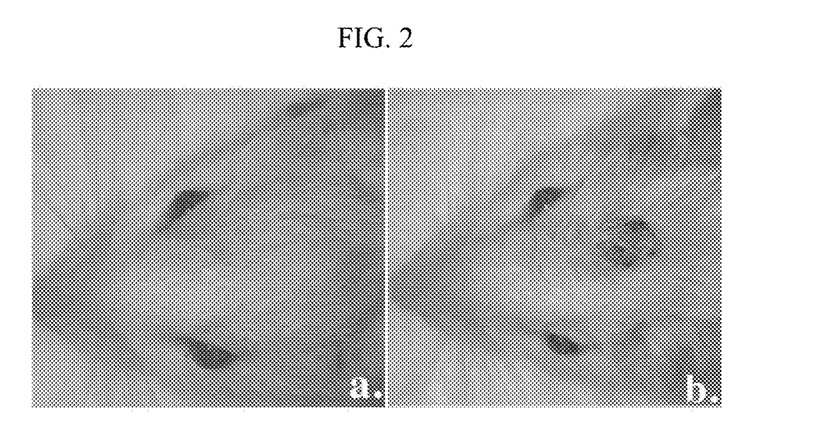
FIG. 2. Scalp closure following craniotomy in rats treated topically with RT175.

Rats which had undergone brain surgery to test RT175 mediated regeneration of the brain following stroke. Following surgery, the scalp was closed. Those rats which had received RT175 treatment achieved full scalp closure. See FIG. 2(a). However, those rats which did not receive RT175 treatment did not achieve scalp closure. See FIG. 2(b).

Example 3. Skin Lesions in Pig Treated Topically with RT175

Figure 3:
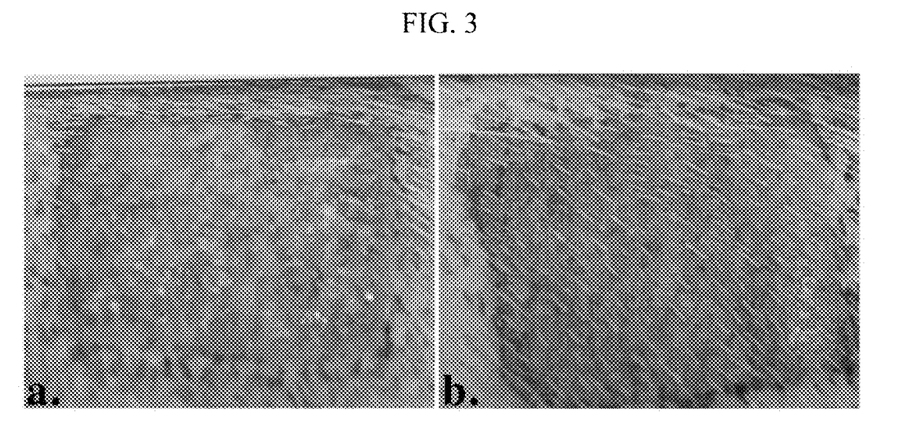
FIG. 3. Skin lesions in pigs treated topically with RT175.

A single pig underwent bilateral, slit thickness, skin surgery leaving lesions on opposite sides of the pig. One of these lesions was then treated topically with 120 ng of RT175, daily. The other lesion was treated with vehicle only. The lesion treated with RT175, and not the lesion treated with vehicle only, exhibited early and transient appearance of granulation tissue, followed by rapid revascularization, invasion of newly formed skin from wound edges, accelerated repigmentation and regeneration of hair. See FIG. 3 and compare 3(b) to 3(a). The de novo hair growth is consistent with the regeneration of the upper hair follicles, most of which would have been removed as the microtome sliced through the skin in creating the split thickness wounds.

Example 4. 59-Year-Old Male with Androgenic Alopecia Treated Topically with RT175 and RT175/Minoxidil A 59-year-old white with androgenic alopecia was treated twice daily with 1 milliliter of a composition containing 120 nanograms/milliliter ("ng/mL") of RT175 in 30% w/v ethanol, 50% w/v propylene glycol and 20% w/v water. The composition was applied directly to the bald skin on the crown of the head once in the morning after showering and once before going to bed. Baseline hair distribution is shown in FIG. 4(a).

Figure 4:
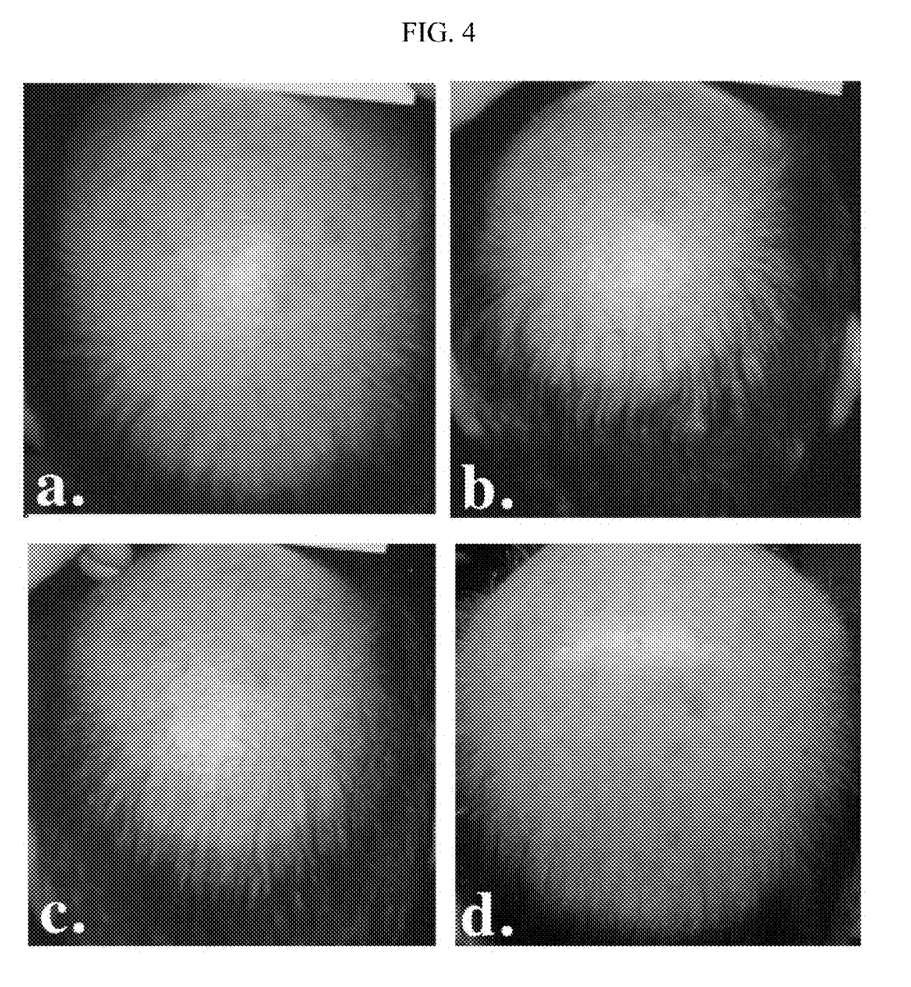
FIG. 4. 59-year-old male with androgenic alopecia treated topically with RT175 and RT175/minoxidil.

FIG. 4(b) shows an absence of hair growth 4 months after RT175 treatment. The subject went on treatment holiday for 1 month, before beginning treatment with 120 ng/mL of RT175 and 5% w/v minoxidil in 30% w/v ethanol, 50% w/v propylene glycol and 20% w/v water. FIG. 4(c) depicts the subjects scalp before initiation of the second round of treatment. FIG. 4(d) shows the failure of the combination of RT175 and minoxidil to induce new hair growth.

Example 5. 57-Year-Old Male with Androgenic Alopecia Treated Topically with RT175/Minoxidil/Cyclosporine A A 57-year-old male with androgenic alopecia was treated twice daily with 1 milliliter of a composition containing 120 ng/mL of RT175 (0.000012% w/v), 1.2 milligrams per milliliter ("mg/mL") of cyclosporine A (0.12% w/v) and 5% w/v minoxidil in about 28% w/v ethanol, about 47% w/v propylene glycol, and about 19% w/v water. The composition was applied directly to the bald skin on the crown of the head once in the morning after showering and once before going to bed. The extent of hair loss is depicted in FIG. 5 in the panel at the upper left (baseline).

Figure 5:
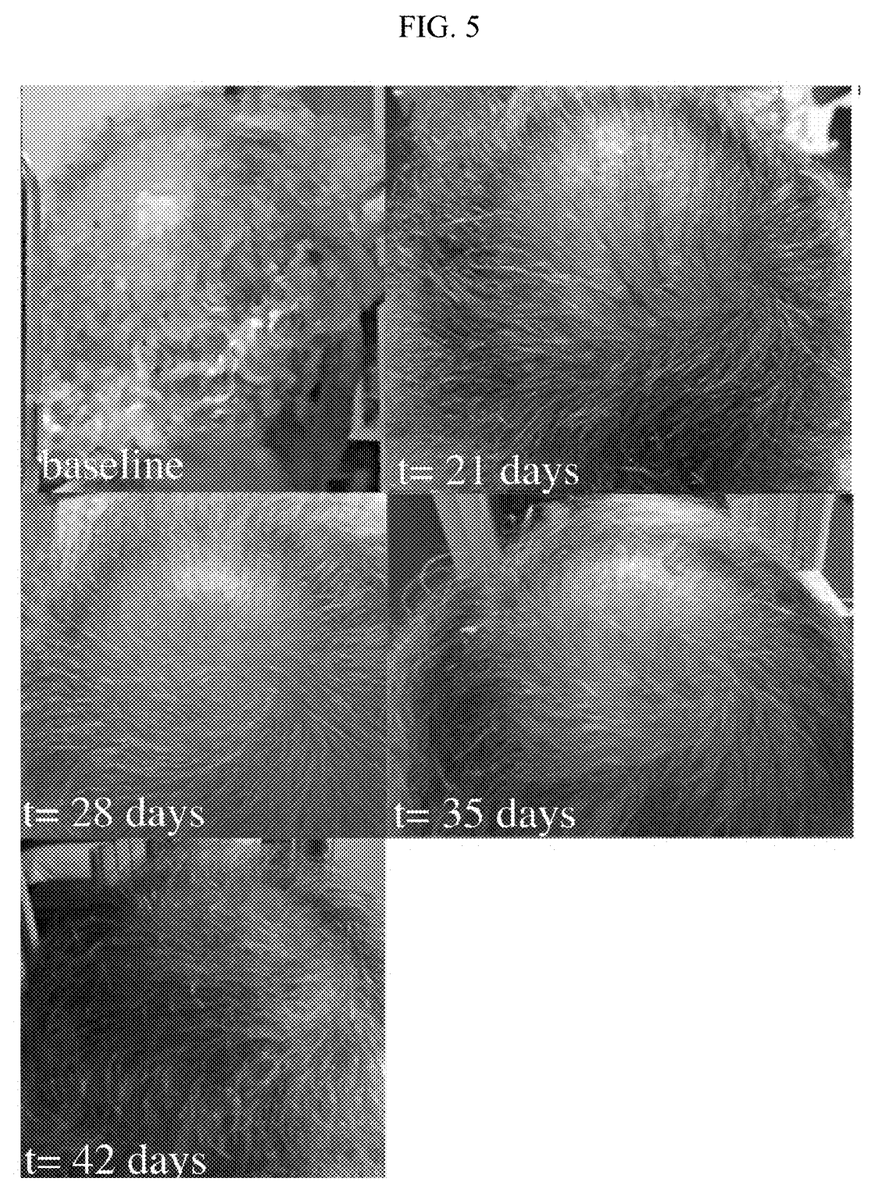
FIG. 5. 57-year-old male with androgenic alopecia treated topically with RT175/minoxidil/cyclosporine A.

FIG. 5 upper right panel shows an unexpected and extensive hair growth after 21 days. FIG. 5 middle left panel shows continued hair growth after 28 days. FIG. 5 middle right panel show continued hair growth after 35 days and lower left panel shows additional hair growth at 42 days. These results are surprising in light of and in stark contrast to the findings in Example 4 that RT175 alone or in combination with minoxidil did not induce new hair growth in a male suffering from androgenic alopecia.

Figure 6:
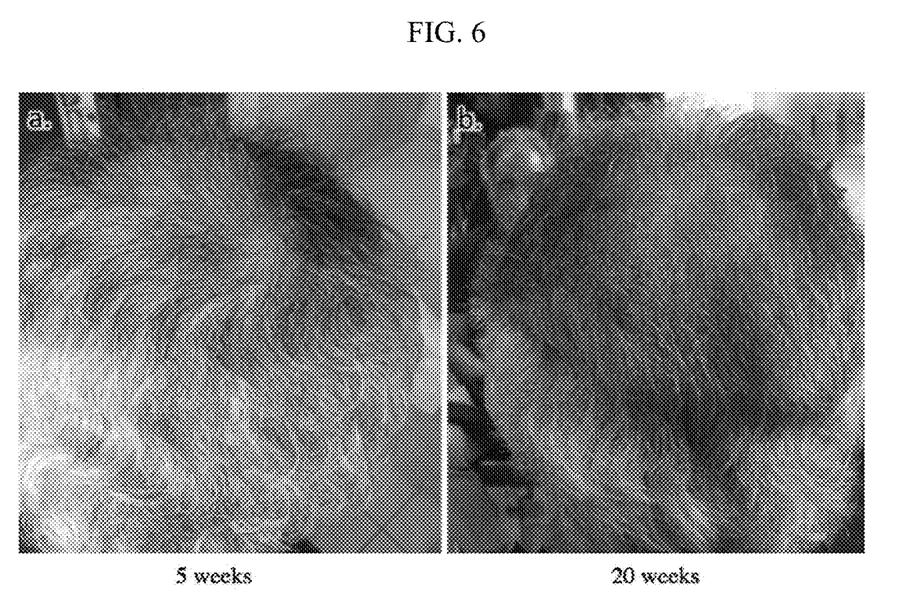
FIG. 6. 57-year-old male with androgenic alopecia and achromotrichia treated topically with RT175/minoxidil/cyclosporine A.

Example 6. 57-Year-Old Male with Androgenic Alopecia and Achromotrichia Treated Topically with RT175/Minoxidil/Cyclosporine a Displays Regrowth of Pigmented Hair A 57-year-old male with androgenic alopecia and who had already gone through achromotrichia (natural loss of pigmentation in the hair follicle and hair shaft) was treated twice daily continuously for 20 weeks with 1 milliliter of a composition containing 120 ng/mL of RT175 (0.000012% w/v), 1.2 milligrams per milliliter ("mg/mL") of cyclosporine A (0.12% w/v) and 5% w/v minoxidil in about 28% w/v ethanol, about 47% w/v propylene glycol, and about 19% w/v water. The composition was initially applied directly to the bald skin at the crown of the head once after showering in the morning and once before going to bed. The composition continued to be applied after robust hair growth. At 5 weeks, the subject began growing pigmented hair in the area of the head where hair loss had occurred. See FIG. 6a. The new pigmented hair of the subject was of a similar color as the subject's hair prior to the subject undergoing achromotrichia. The hair outside of the treated area did not develop pigment. By the 20th week of treatment, there was extensive growth of pigmented hair over the totality of the treated area. See FIG. 6b. This result demonstrates that the composition of the invention not only regrows hair in patients with androgenic alopecia but also regrows pigmented hair in patients with androgenic alopecia who have undergone achromotrichia due to aging.

Example 7. Prophetic Combination Treatment of Alopecia with Fractional Laser Treatment and Topical Minoxidil, Cyclosporine a or RT175

Method

Subject 1, a 50-year-old male, was subjected to topical administration of RT175, once in the morning after showering and once before going to bed for 60 days. After 30 days-post treatment Subject 1 had not experienced significant hair regrowth. 60 days-post RT175 treatment Subject 1 was subjected to Fraxel® fractional laser treatment of areas of the scalp affected by alopecia using standard Fraxel® protocol. 45 day-post Fraxel® treatment Subject 1 had not experienced substantial hair regrowth. 7 days later, Subject 1 was retreated with Fraxel® followed 8 hours later by topical treatment with a composition containing RT175. Subject 1 then continued topical treatment with the RT175 composition for 60 days.

Results

On day 21-post Fraxel®/RT175 treatment, subject 1 began regrowing hair in areas of the scalp affected by alopecia. This regrowth continued through the end of the treatment on day 90. Example 8. 24-year-old male with inadequate facial hair growth treated topically with RT175/minoxidil/cyclosporine A displays enhanced growth of facial hair.

Figure 7:
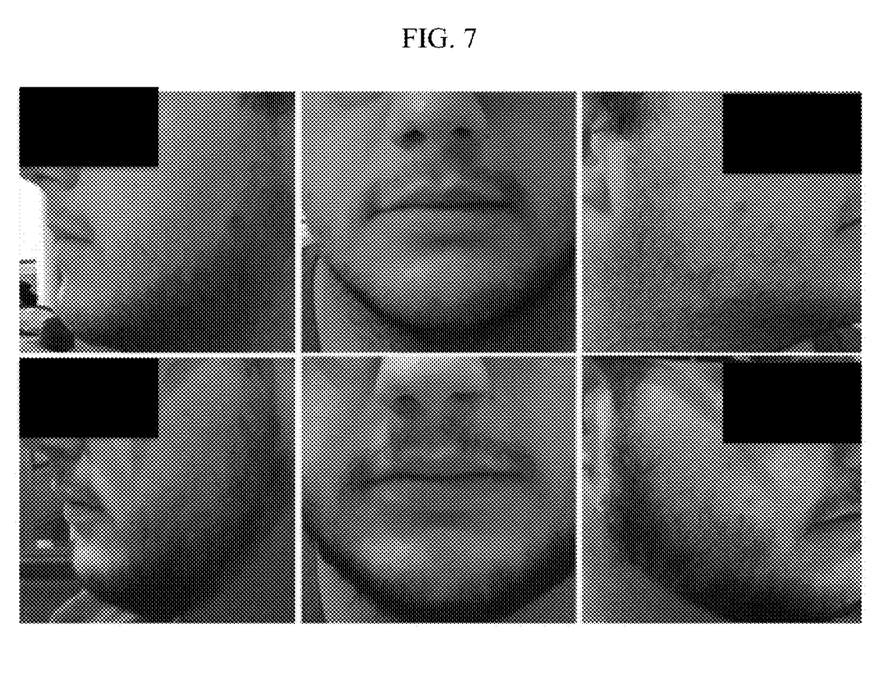
FIG. 7. 24-year-old male with inadequate facial hair growth treated with RT175/minoxidil/cyclosporine A.

A 24 year old male with inadequate facial hair growth was treated twice daily for three weeks with 0.4 milliliter of a composition containing 120 ng/mL of RT175 (0.000012% w/v), 1.2 milligrams per milliliter ("mg/mL") of cyclosporine A (0.12% w/v) and 5% w/v minoxidil in Vanicream® (Vanicream is a registered trademark of Pharmaceutical specialties, Inc. and contains white petrolatum, sorbitol solution, propylene glycol, cetearyl alcohol, ceteareth-20, simethicone, glyceryl monostearate, polyethylene glycol monostearate, sorbic acid and butylated hydroxytoluene). FIG. 7, upper panels, shows baseline facial hair. FIG. 7, lower panels, shows facial hair following three weeks of twice daily treatment with RT175/cyclosporine A/minoxidil.

Example 8. Treatment of Dermabrasion Lesions of Dorsal Skin of Mice with RT175 Analog, RT1061

Retired ICR breeder mice of both sexes with weight between 45 and 50 grams were shaved and rasped to induce dermabrasion lesions. The animals were then randomly assigned (5 per treatment arm) to one of two groups to receive either 5 μL of 100 nanomolar RT1061 or a vehicle control. RT1061 or vehicle control was applied topically to the lesion site once each day including immediately after dermabrasion.

Figure 8:
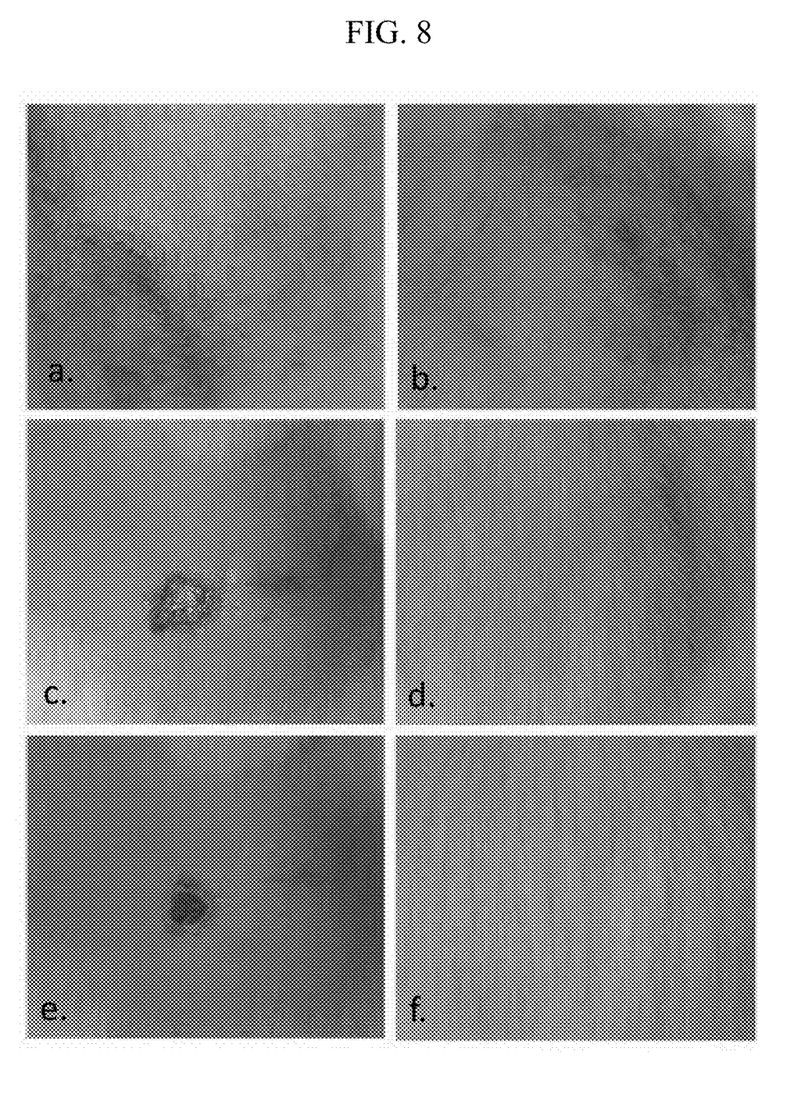
FIG. 8. Skin regeneration and hair regrowth following shaving and rasping of mice dorsal skin and 10-day treatment with RT1061.

Results of the study can be seen in FIG. 8. As shown, treatment with RT1061 (panels b., d. and f.) resulted in rapid hair growth and rapid regeneration of rasped skin. In contrast, treatment with the control vehicle resulted in scab formation and no hair regrowth 10 days after rasping. See FIG. 8, panels a., c. and e.

What is claimed is:

1. A composition for the treatment of alopecia comprising 0.000012% w/v of a compound of formula (II)

(II)

or a pharmaceutically acceptable salt or ester thereof, 5% w/v minoxidil, 0.12% w/v cyclosporine A, 28% w/v ethanol, 47% w/v propylene glycol and 19% w/v water, wherein w/v denotes weight by volume.

2. The composition of claim 1 further comprising one or more excipients selected from the group consisting of urea, polyoxyl 40 stearate, a carbomer, cetyl alcohol, glyceryl monostearate, mineral oil, polyglycol 300, citric acid, sodium phosphate dibasic, stearyl alcohol, isopropyl myristate, sodium hydroxide, petroleum jelly, xanthan gum, white petrolatum, sorbitol solution, cetearyl alcohol, ceteareth-20, simethicone, sodium benzoate, glyceryl monostearate, polyethylene glycol monostearate, sorbic acid, and butylated hydroxytoluene.

3. A method of treating alopecia comprising topically administering to a human in need thereof an effective amount of the composition of claim 1.

4. A method of treating achromotrichia comprising topically administering to a human in need thereof an effective amount of the composition of claim 1.

5. The method of claim 3 wherein the achromotrichia is due to aging.

6. A method of enhancing facial hair growth comprising topically administering to a human in need thereof an effective amount of the composition of claim 1.

7. A method of treating alopecia in a human in need thereof comprising the steps of:
   (i) administering fractional laser treatment to an affected area of a human; and
   (ii) topically administering a composition of claim 1.

8. A method of treating alopecia in a human in need thereof comprising the steps of:
   (i) pretreating an area affected with alopecia with 40% w/v urea; and
   (ii) topically administering a composition of claim 1, wherein w/v denotes weight by volume.

* * * * *